(12) United States Patent
Hanson et al.

(10) Patent No.: US 12,135,319 B2
(45) Date of Patent: Nov. 5, 2024

(54) ELECTRICAL IMPEDANCE SPECTROSCOPY FOR NON-DESTRUCTIVE, REAL-TIME, TRACKING OF RELATIVE WATER CONTENT AND STRESS RESPONSES IN PLANTS

(71) Applicants: David Hanson, Albuquerque, NM (US); Patrick Joseph Hudson, Albuquerque, NM (US); Kaitlyn Johanna Hughes Read, Albuquerque, NM (US); Laura Green, Albuquerque, NM (US); Joseph Stinziano, Albuquerque, NM (US); Tito Busani, Albuquerque, NM (US); Mahmoud Behzadirad, Albuquerque, NM (US)

(72) Inventors: David Hanson, Albuquerque, NM (US); Patrick Joseph Hudson, Albuquerque, NM (US); Kaitlyn Johanna Hughes Read, Albuquerque, NM (US); Laura Green, Albuquerque, NM (US); Joseph Stinziano, Albuquerque, NM (US); Tito Busani, Albuquerque, NM (US); Mahmoud Behzadirad, Albuquerque, NM (US)

( * ) Notice: Subject to any disclaimer, the term of this patent is extended or adjusted under 35 U.S.C. 154(b) by 293 days.

(21) Appl. No.: 17/599,085

(22) PCT Filed: Mar. 30, 2020

(86) PCT No.: PCT/US2020/025710
§ 371 (c)(1),
(2) Date: Sep. 28, 2021

(87) PCT Pub. No.: WO2021/002900
PCT Pub. Date: Jan. 7, 2021

(65) Prior Publication Data
US 2022/0163499 A1    May 26, 2022

Related U.S. Application Data

(60) Provisional application No. 62/913,263, filed on Oct. 10, 2019, provisional application No. 62/825,396, filed on Mar. 28, 2019.

(51) Int. Cl.
| | | |
|---|---|---|
| *G01N 33/00* | (2006.01) |
| *A01G 7/00* | (2006.01) |
| *G01N 27/22* | (2006.01) |

(52) U.S. Cl.
CPC ........... *G01N 33/0098* (2013.01); *A01G 7/00* (2013.01); *G01N 27/223* (2013.01)

(58) Field of Classification Search
None
See application file for complete search history.

(56) References Cited

U.S. PATENT DOCUMENTS 3,967,198 A * 6/1976 Gensler ............... A61B 5/24
324/692
5,224,769 A * 7/1993 Holbrook ........... G01N 33/0098
47/1.01 R (Continued)

FOREIGN PATENT DOCUMENTS

CN    116075217 A  *  5/2023

OTHER PUBLICATIONS

Jamaludin et al, Impedance Analysis of Labisia Pumila Plant Water Status, Jul. 24, 2015, Information Processing In Agriculture 2, pp. 161-168 (Year: 2015).*

(Continued)

*Primary Examiner* — Jermele M Hollington
(74) *Attorney, Agent, or Firm* — Henry D. Coleman

(57) ABSTRACT

Methods and apparatus for electrical impedance spectroscopy for non-destructive, real-time, tracking of relative water content and stress responses in plants.

11 Claims, 8 Drawing Sheets

(56) References Cited

U.S. PATENT DOCUMENTS

| 6,870,376 | B1 * | 3/2005 | Gensler | A01G 25/167 |
| | | | | 324/663 |
| 10,921,303 | B1 * | 2/2021 | Dong | G01N 27/4145 |
| 11,060,989 | B2 * | 7/2021 | Hanson | G01N 27/026 |
| 11,143,534 | B2 * | 10/2021 | Lee | G01N 33/0098 |
| 11,740,113 | B2 * | 8/2023 | Lee | G01F 1/692 |
| | | | | 73/204.22 |
| 2017/0010296 | A1 * | 1/2017 | Shimokawa | A01G 7/00 |
| 2019/0257681 | A1 * | 8/2019 | Lee | G01F 1/69 |
| 2023/0304952 | A1 * | 9/2023 | Shimokawa | G01N 27/048 |

OTHER PUBLICATIONS

Mizukami et al, Moisture Content Measurement of Tea Leaves by Electrical Impedance and Capacitance, Feb. 7, 2006, Biosystems Engineering 93, pp. 293-299 (Year: 2006).*

Jeon et al, Real-time Monitoring of Electroconductivity in Plants with Microscale Needle Probes, Jan. 11, 2018, Environment Control in Biology, 56(4), pp. 131-135 (Year: 2018).*

Jeon et al, Development of Electrical Conductivity Measurement Technology for Key Plant Physiological Information Using Microneedle Sensor, Jul. 20, 2017, Journal of Micromechanics and Microengineering, 27(8), pp. 1-9 (Year: 2017).*

Anonymous, Improved disposable sensor for detecting fluid and new connection clip adapted to said sensor, Feb. 3, 2012, IP.com (Year: 2012).*

Bar-On et al, Four Point Probe Electrical Spectroscopy Based System for Plant Monitoring, 2019, IEEE (Year: 2019).*

Ino et al, Microsensor Device for Minimally Invasive Measurement of Moisture Storage in Plants Shoots, 2020, IEEE (Year: 2020).*

* cited by examiner

ELECTRICAL IMPEDANCE SPECTROSCOPY FOR NON-DESTRUCTIVE, REAL-TIME, TRACKING OF RELATIVE WATER CONTENT AND STRESS RESPONSES IN PLANTS

CROSS-REFERENCE TO RELATED APPLICATIONS

The following application claims benefit of U.S. Provisional Application Nos. 62825396, filed Mar. 28, 2019, and 62/913,263, filed Oct. 10, 2019, each of which is hereby incorporated by reference in its entirety.

STATEMENT REGARDING GOVERNMENT SPONSORED RESEARCH

This invention was made with Government support under Grant No. DEB 1737899 awarded by the National Science Foundation and Grant No. DE-AR0000829 awarded by the Advanced Research Projects Agency for Energy. The U.S. Government has certain rights in this invention.

BACKGROUND

Plant water status is a universal signal that governs plant physiology, controlling photosynthesis, growth, and productivity, but it is hard to measure and monitor. For example, plant relative water content plays a large role in determining plant function, both before and after damage occurs. Moreover, all aspects of plant productivity are directly or indirectly linked to plant water status. Plant carbon capture depends on a sufficient supply of soil moisture to replenish water lost by evaporation from leaves, this carbon provides the fundamental building blocks of plant cells and metabolites. Plant growth depends on cell division and cell expansion, and these processes require maintenance of cell pressure (like tire pressure) that is only possible with high levels of hydration. Plants that even approach wilting (loss of pressure) are unhealthy. In addition, biochemical pathways are turned on and off at species specific water statuses. This is why many crops receive some drought stress on purpose to enhance flavor and quality (spiciness of New Mexico chile is a good example since spiciness is a stress/defense response).

Moreover, a plant's relative water content and mechanisms for responding thereto are highly variable between different plant species and can evolve rapidly. For example, bryophytes and desiccation tolerant plants have little to no ability to control water loss See e.g., Black M, Pritchard H W, eds. 2002. Desiccation and survival in plants. Drying without dying. Wallingford, UK: CABI Publishing. 412 pp. which is hereby incorporated by reference for all purposes.). Relative water content can be very high in mosses like Sphagnum, where a water film develops over photosynthetic tissue and is a barrier to carbon dioxide diffusion into the leaf, then rapidly dries, passing through optimal conditions down to low levels where drying stress causes changes in membrane properties to impair physiology, and even go so low that there is insufficient water for metabolism. Progressing rapidly from optimal to very low water (equilibrated with air water vapor) is a strategy of desiccation tolerant plants (Black and Pritchard, 2002). The speed of this change makes it hard to track and then correlate relative water content with physiological traits. This then makes it hard to separate out effects of drying stress from all other stresses including temperature and light stress. Similar challenges exist for other plants and algae that dry more slowly because current methods do a poor job on any time scale without destructive sampling.

Currently, standard practices of growers do not even assess plant water status. Instead they infer plant water status from soil sensors (FIG. 1), because reliable continuous plant sensors do not exist. With soil sensors, growers must decide how deep their plants roots will grow and if they also want to measure shallow soil for young plants. In addition, they need to understand how their soils vary in factors like water holding capacity, ease of wetting, and proximity to water tables, as well as how their crops roots interact with soils and microorganisms. This can best be done when conditions and crop varieties are consistent, but weather is inherently variable and climates are changing. If the plant water status is measured, then most of these uncertainties disappear and new kinds of information about plant health can be captured and easily interpreted.

In a laboratory setting, measurement of relative water content can be facilitated by continuously weighing samples as they lose water, but that is impractical to impossible in the field.

Moreover, standard measurement typically requires removal of some portion of the plant body, generally a leaf or twig, which only works for some species and often causes severe damage to young or small plants.

Standard practices of breeders and scientists involve the consideration of plant water status from two perspectives: water potential, and relative water content. Water potential represents the force a plant must endure to extract water from soil. Relative water content compares the water content of a plant sample at a specific time to the maximum water content the plant can achieve. Neither of these parameters are easily measured, either in the laboratory or the field. Both require specialized equipment and training and are difficult or impossible to scale for rapidly processing large numbers of samples.

Accordingly, the transition from discrete, damaging sampling to continuous, minimally invasive sampling represents a profound advancement of plant monitoring capability in both the laboratory and real world settings.

SUMMARY

According to various embodiments, the present disclosure provides methods and apparatus for electrical impedance spectroscopy for non-destructive, real-time, tracking of relative water content and stress responses in plants.

DETAILED DESCRIPTION

According to an embodiment the present disclosure provides methods and apparatus for electrical impedance spectroscopy for non-destructive, real-time, tracking of relative water content and stress responses in plants.

In general, the present disclosure provides a low-cost, easily used sensor to directly monitor plant health in both laboratory and real-world settings. The device uses the electrical properties of plants as a screen for water status as well as other properties, including cell damage and sugar content. The presently described sensor provides easy-to-interpret data continuously and with minimal superficial damage to the plant, thus offering the unparalleled ability to monitor plant water use and demand, as well as plant health. The technology depends on electrical impedance spectroscopy (EIS), a non-destructive methodology used for characterizing materials and biological systems by studying frequency-dependent impedance signals. The presently described approach to EIS is unique in at least the following ways: 1) it uses novel nanowire microprobes to target specific cells and tissues, but is not limited to use with nanowire probes, 2) impedance measurements at multiple frequencies provide a more useful signal about plant water status and sugar content than single frequencies, and 3) phase-angle analyses to assess plant tissue health, including membrane integrity and ion leakage. These signals can then be directly monitored to control watering as well as nutrient addition, and even be used for environmental control for indoor agriculture. In addition, the signals can be correlated with metabolite composition, flavor profiles, and other desirable properties of living or harvested tissues to improve the repeatability of plant product production. The sensors have been validated in lab and field conditions. According to specific embodiment, the present disclosure contemplates a system including a probe which is attached to a plant in order to take impedance measurements and an impedance analyzer with data logging and user-interface functionality.

For the purposes of the present disclosure, the term "microprobe" is intended to mean a physical structure which is conductive at the tip and is sufficiently small to only contact the desired cells or tissues. According to a specific embodiment, the novel nanowires described herein achieve this by placing a small conductive tip (tens of nanometers to tens of micrometers in diameter, on top of a non-conductive base. Examples of microprobes include, but are not necessarily limited to microneedles, nanowires, and other small wires or conductive materials.

Figure 1:
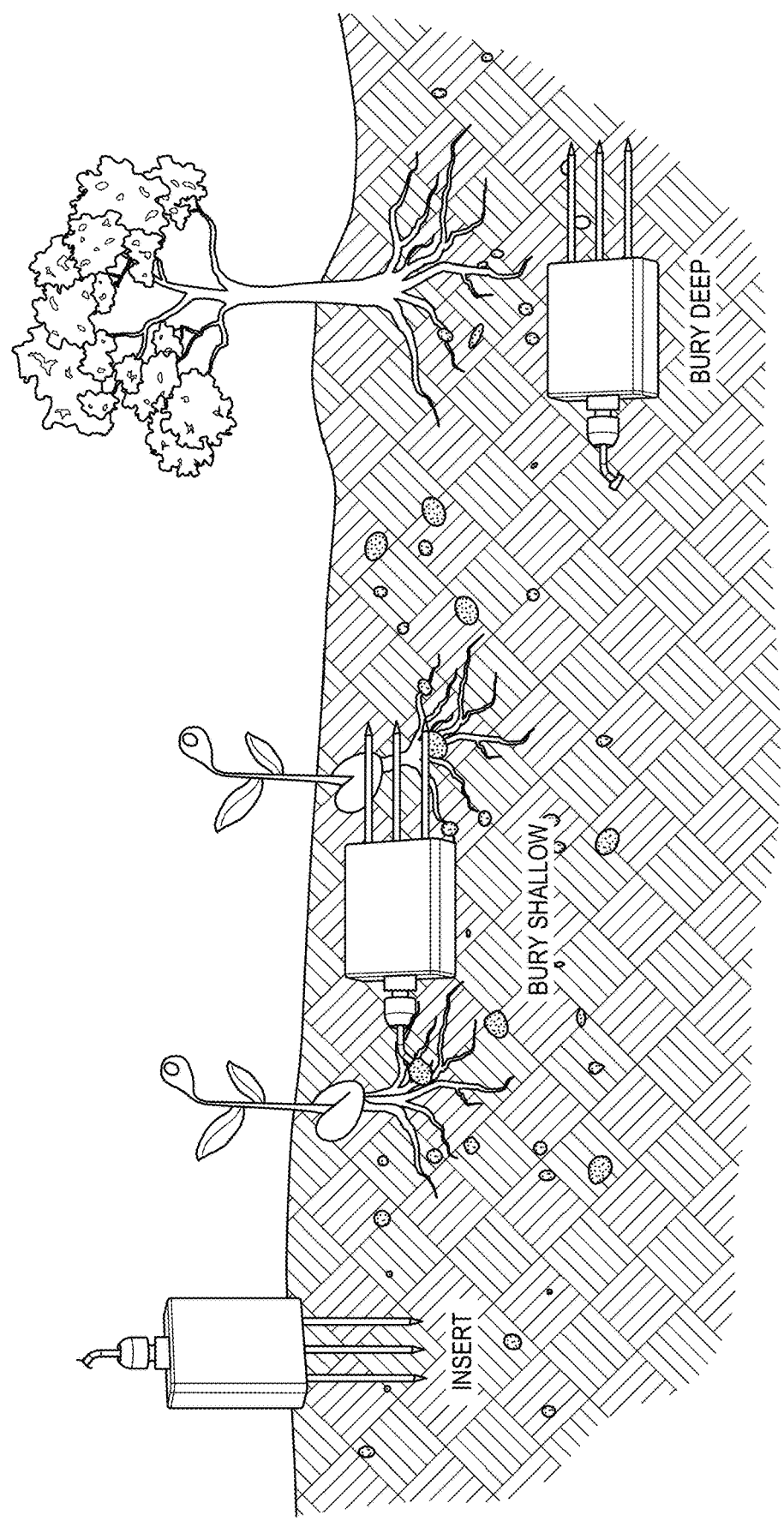
FIG. 1 is a schematic illustration demonstrating that the value of soil sensors is affected by where they are placed and soil uniformity. If a plants roots are getting water from soil far from the soil sensor then the data will not be useful. In contrast, sensors placed on the plant will always report relevant information.
Figure 2:
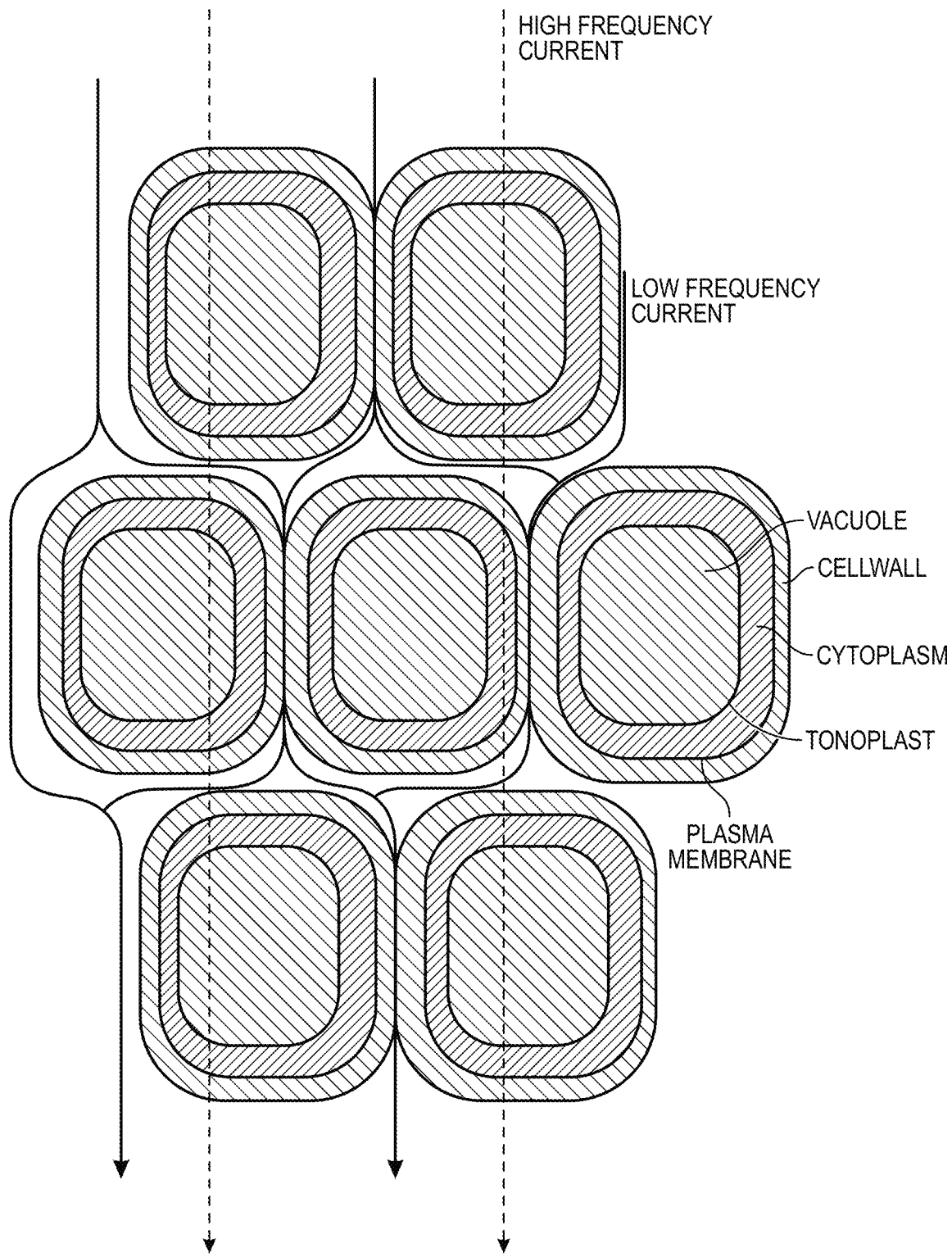
FIG. 2 provides a simplified model of plant tissue, and the conductance pathways of low (solid lines) and high (dashed lines) frequency currents used in EIS.

EIS uses alternating electrical current applied over a range of frequencies to assess the passive electrical properties of a material. The method is nondestructive, as the current applied has low voltage. EIS provides two primary pieces of information characterizing a material: impedance and phase angle. Impedance essentially describes the resistance to the electricity and varies with the frequency of applied voltage and the chemical and physical properties of the material. Phase angle describes the tendency of a material to behave as a resistor or a capacitor. All cells are bound by plasma membranes, which act as capacitors when they are intact. Plant cells are also surrounded by cell walls that are essentially fibers surrounded by a gel containing water, ions, and other compounds. The concentrations of ions inside and outside of cells dictates the electrical properties of those compartments. Low frequency currents cannot pass through plasma membranes, so they only measure the electrical properties in the cell wall space, whereas high frequency currents pass through cell membranes and cell walls, measuring both cell and cell wall compartments (FIG. 2).

Figure 3:
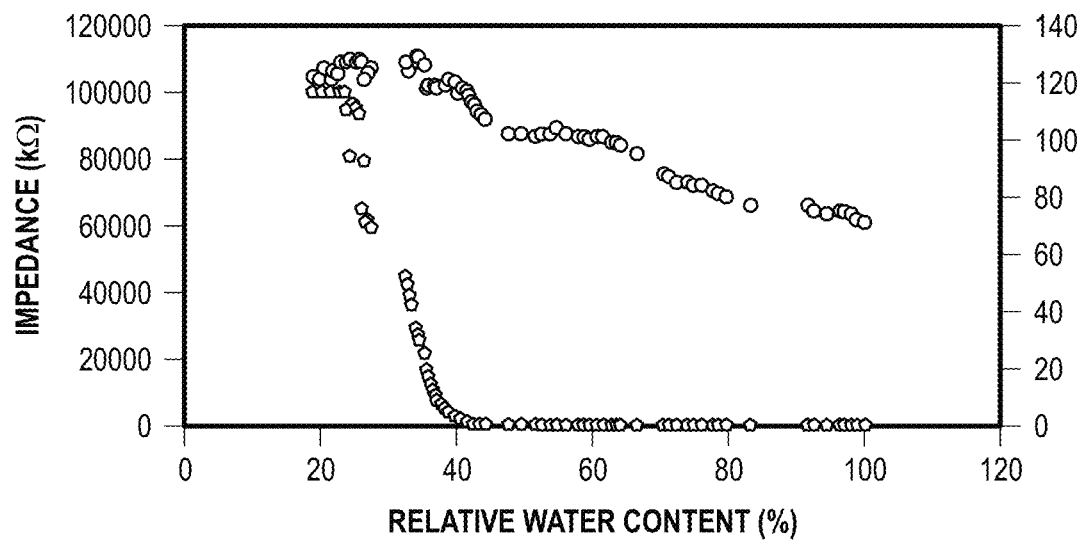
FIG. 3 is a graph showing that high frequency impedance (light grey) and low frequency impedance (black) respond differently to plant relative water content and in a species specific manner Utilizing both frequencies together refines the signal by correcting for background effects on single frequency measurements.

We have discovered that there is a close relationship between plant relative water content and impedance. As demonstrated in FIG. 3, Both low frequency and high frequency impedance have a negative correlation with water content, such that, as relative water content decreases (i.e., water stress increases), impedance increases. The relationship is frequency dependent (FIG. 3) where low frequencies are informative about extra-cellular water and water in cell wall spaces whereas high frequency values are also impacted by water within cells. Comparing responses at multiple frequencies thus helps separate cellular versus intercellular water content.

Figure 4:
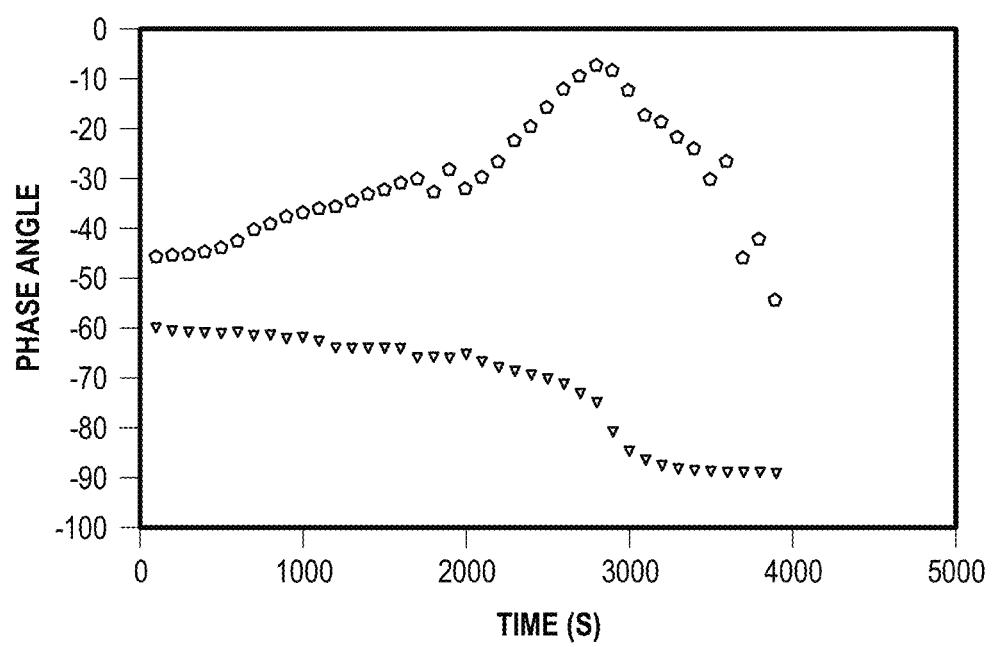
FIG. 4 is a graph that uses the data shown in FIG. 3, but calculating phase angle with time after the start of tissue drying. Phase angle is used as a way to assess cell membrane capacitance and the since high (light grey) frequencies pass through cell membranes and low (black) frequencies do not, the high frequency data changes are used to refine the low frequency signals in order to refine assessments of membrane integrity (plant tissue health).

Furthermore, by mathematically transforming multiple frequencies, the system of the present disclosure can distinguish between intra and intercellular capacitance (via phase angle analyses), which is a measure of membrane integrity. This is critical because loss of membrane integrity is a major stress response to water, temperature, and even light stress. Therefore, the presently described technology can distinguish between relative water content limitations and changes in membrane function. Similar to impedance, phase angle responses are frequency dependent (FIG. 4) and using multiple frequencies can correct for changes in resistance due to water content changes in order to refine our analysis of cell membrane integrity (tissue health). These relationships enable the presently disclosed device to accurately measure and monitor plant tissue water content and health in real-time and over multiple days.

Figure 5:
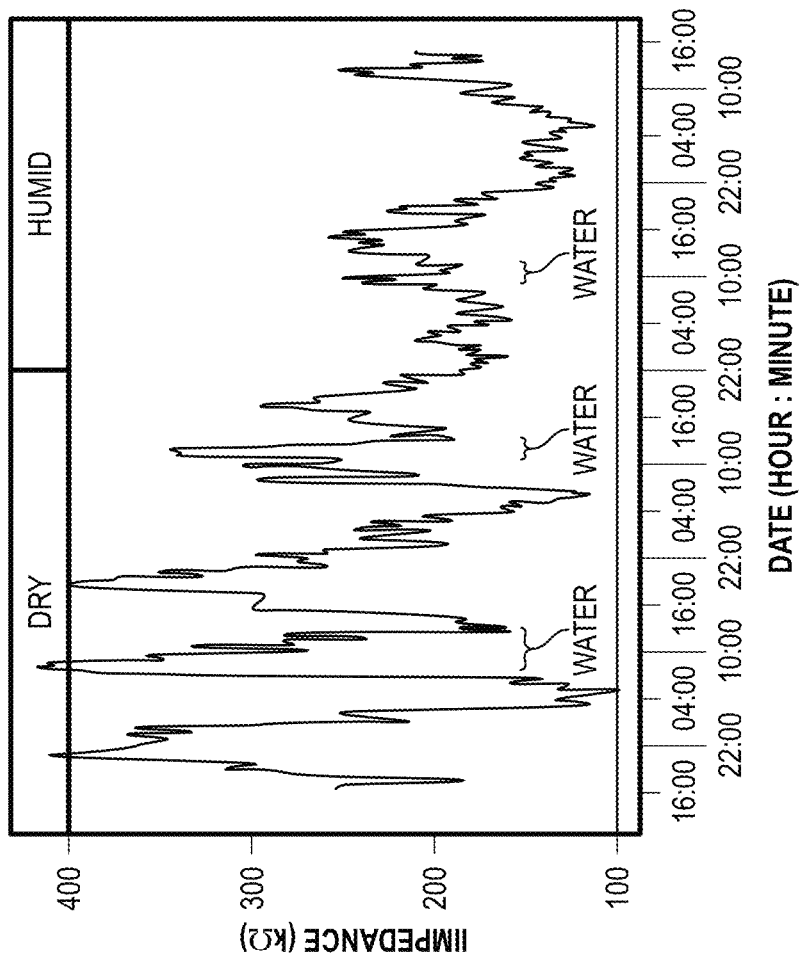
FIG. 5 is a graph depicting cycles of impedance recorded from a *Sorghum bicolor* leaves over four days in a greenhouse. Impedance patterns replicate expected daily cycles of leaf evaporation and water content (correlate positively with light, temperature, and humidity). Dips occur when plants were watered, and low values were observed when the air was humid and more clouds were present (both reducing evaporation). Greyscale bar at the bottom represents day (light grey) to night (black) changes in light intensity.

FIG. 5 shows cycles of impedance recorded from a *Sorghum bicolor* leaves over four days in a greenhouse. Impedance patterns replicate expected daily cycles of leaf evaporation and water content (correlate positively with light, temperature, and humidity). Dips occur when plants were watered, and low values were observed when the air was humid and more clouds were present (both reducing evaporation). The greyscale bar at the bottom represents day (light coloring) to night (dark coloring changes in light intensity.

Figure 6A:
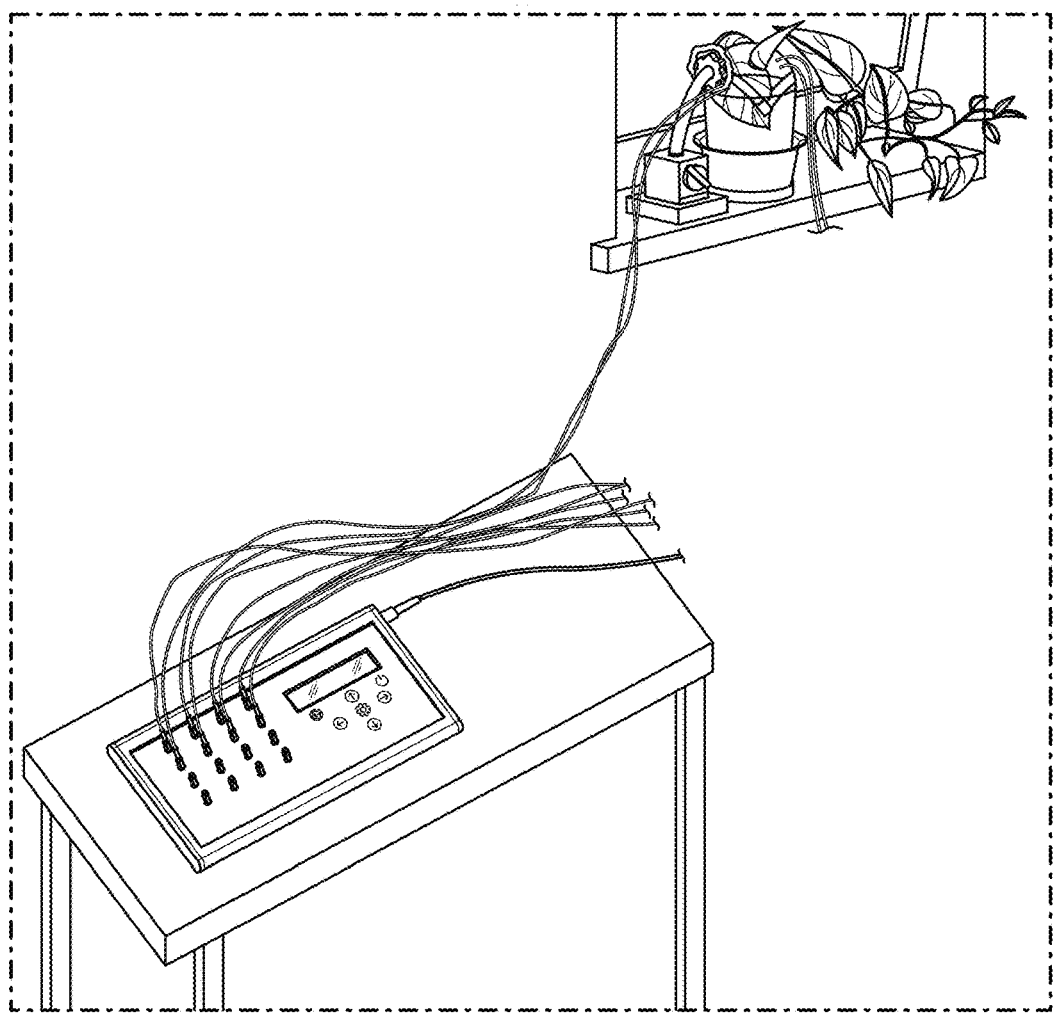
FIGS. 6A-6D depicts an exemplary multi-channel plant impedance probe (multi-PIP) according to an embodiment of the present disclosure analyzer is shown in the upper left (FIG. 6B) and also centrally connected to a plant in the window of the central image (FIG. 6A). Probes are shown connected to a delate leaf edge (middle right) (FIG. 6C) and a strong central leaf midrib (bottom right) (FIG. 6D).
Figure 6B:
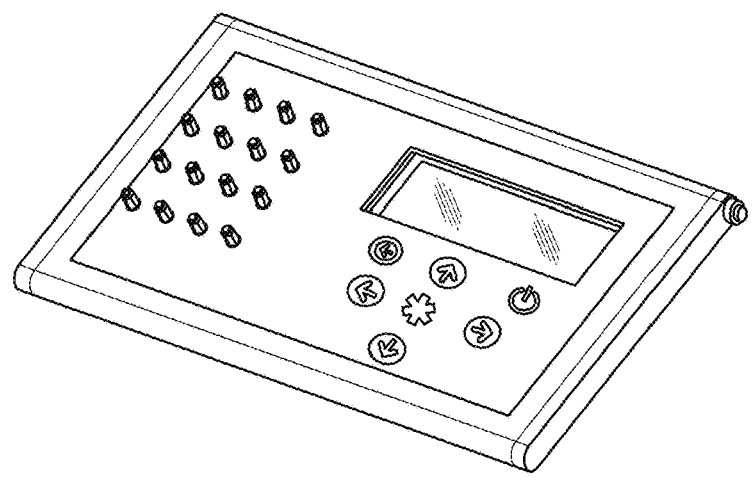
Figure 6C:
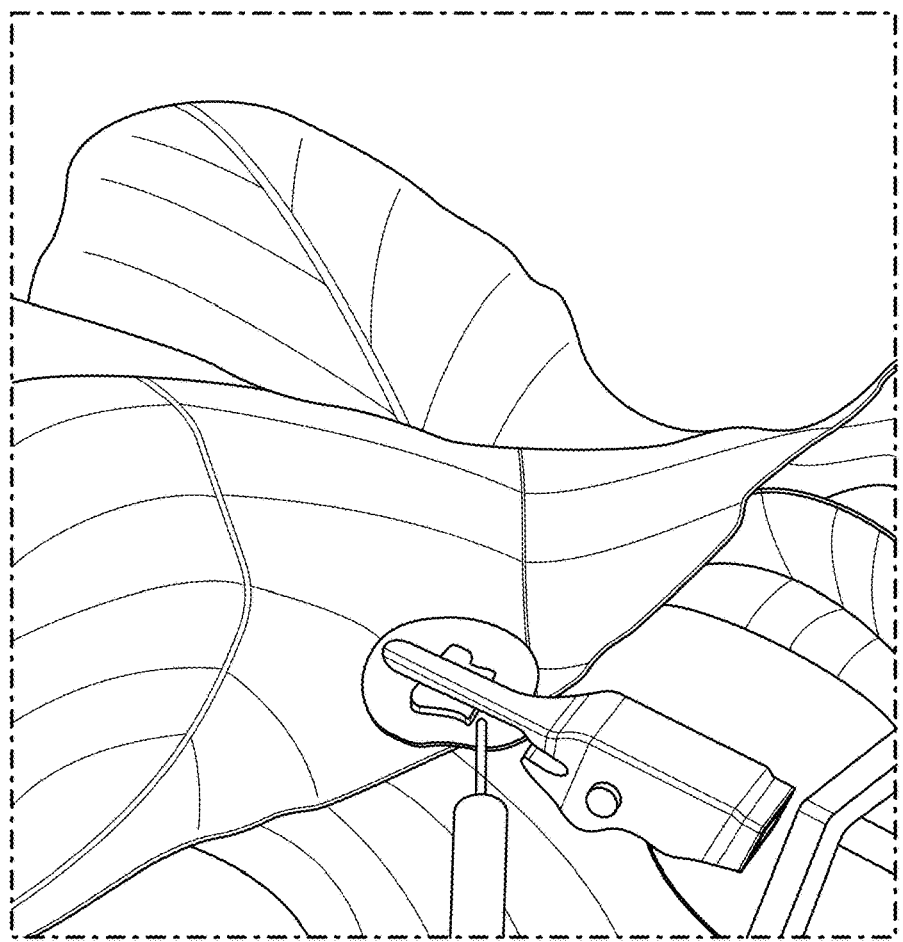
Figure 6D:
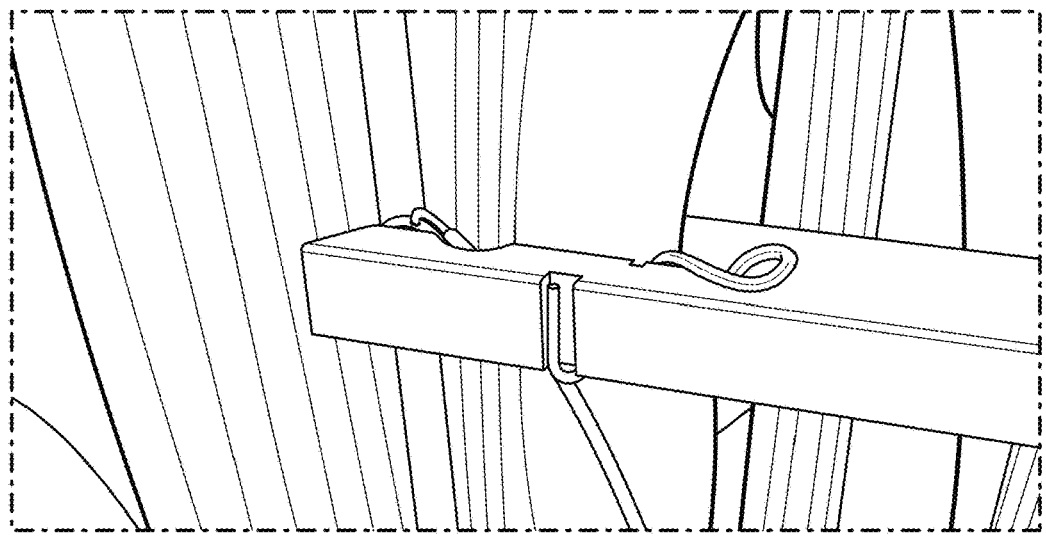

In general, as demonstrated in FIGS. 6A-6D the system of the present disclosure includes a probe having body which can be either permanently or reversibly affixed to a plant (FIGS. 6C, 6D). The type of attachment and location of the plant to which the body is affixed is typically determined by the specific plant being monitored. For example, plants with large strong leaves like sorghum may be amenable to attachment on the leaf lamina or mid-rib while other plants like moss or *Arabidopsis thaliana* with delicate and easily damaged leaf structures may be more amenable to attachment to a branch, stem, or petiole. Attachment mechanisms may include clips, magnets, elastic bands, custom 3D printed devices, or adhesives.

The body may further comprise one or more microprobes which measure the impedance of the plant. The body may have a unilateral design that includes both the attachment mechanism and the microprobe(s) or may comprise one or more microprobes which extend from of are otherwise in physical communication with the body.

According to a first embodiment, the microprobes may take the form of microneedles.

Alternatively, the microprobes may take the form of nanowires or nanostructured semiconductors. For example, gallium nitride (GaN) nanowires (NWs), which exhibit unique properties such as a high bending strength and excellent mechanical properties, high chemical stability, tunable electrical properties, and can be fabricated different geometry with different approaches though mass production at low costs. Further, GaN is a material that can be fabricated in high aspect ratio structures with a transverse dimension or effective diameter of from 10 nanometers (nm) to tens of microns and with almost perfect crystal facet sidewalls with lengths ranging from 100 nm to 10 micrometers (μm). These NWs can be fabricated through either a top-down approach with a flat top, or a bottom-up approach with a sharp apex or a flat top.

Figure 7:
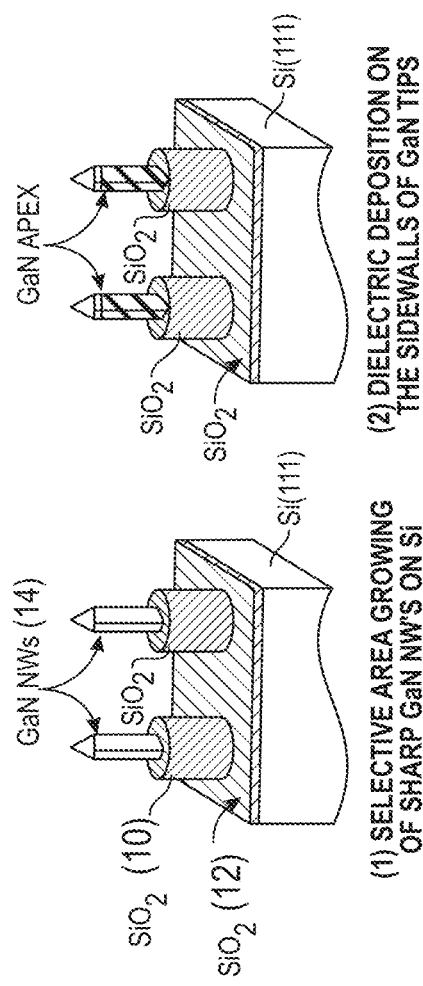
FIG. 7 is a schematic illustration of an exemplary fabrication process for GaN tip-based plant health sensors.
Figure 7:
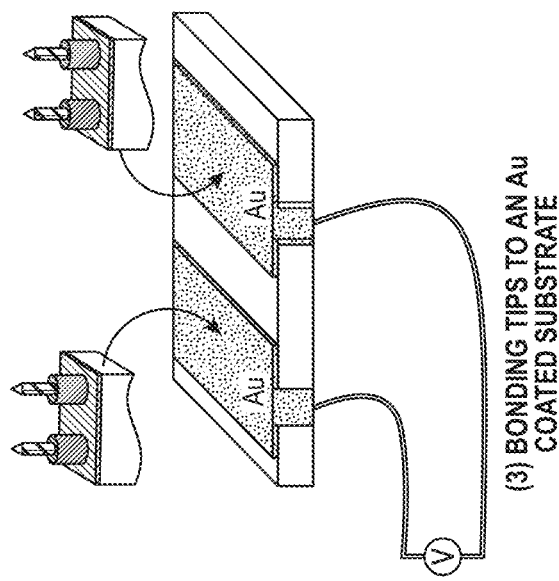
Figure 8:
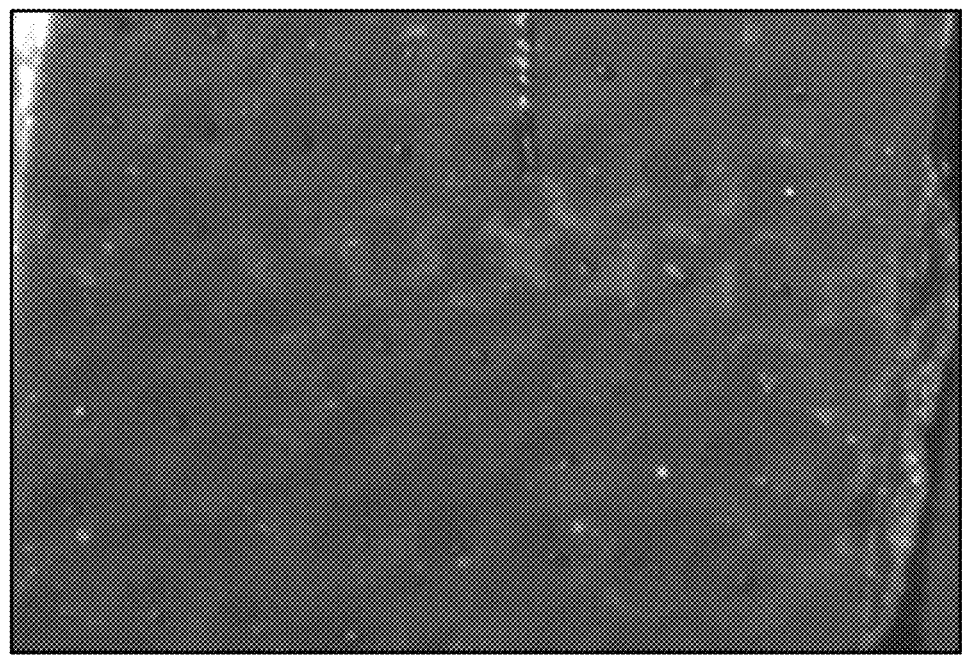
FIG. 8 shows an array of nanowire tips on a conductive surface for use on plants tissues (upper panel).
Figure 9:
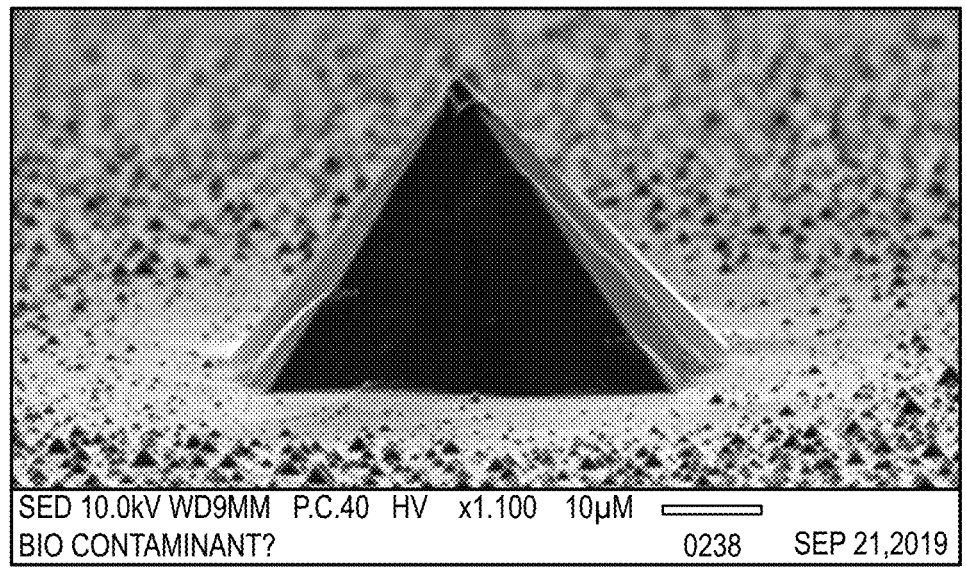
FIG. 9 is an SEM image of a single nanowire tip (bottom panel) on from the array in the upper panel.

According to a specific embodiment, a bottom-up approach to growth GaN NW tips on Si substrate as previously disclosed in our patent ("Rugged, single crystal wide-band-gap-material scanning-tunneling-microscopy/lithography tips." U.S. patent application Ser. No. 16/095,011, now U.S. Patent No.). Briefly, as shown in FIG. 7 the process is started with creating a mesa (or needle body) (10) with about ~30-50 μm height on a Si substrate (12). The mesas are patterned by dielectric material (e.g. SiO2, SiNx) to enable selective area growth of GaN NWs (14) on top of the mesas. Then NW sidewalls are also patterned by a dielectric and the apex of the tip is left pristine to enable current flow. Finally, fabricated tips are bonded to a gold coated substrate to enable applying bias to the tips. FIG. 8 shows an array of nanowire tips not on a raised base. These are used for the most shallow measurements of surface cells on plant tissues.

These novel nanowire probes fabrication have the advantage of manufacturing nanowires that only being conductive at the tips and they can easily be designed to penetrate to different critical depth in a tissue by changing the dimensions of the Si base. In addition, individual probe tips in a small patch can be independently measured, greatly improving our ability to test for connectivity and compare tissues. Other probes and needles are conductive along their full length which reduces tissue and cell type specificity.

As stated above, the system may further include a device (FIGS. 6A, 6B) which receives the impedance data from probe and delivers the data to a user. This device may take the form, for example, of a handheld device which a user can manipulate in order to obtain the data from the probe. For example, the device may communicate in either a wired or wireless fashion (using, for example, Bluetooth or other know wireless communication means) with the probe. Such communication may only occur when the device is within specific proximity of the probe (i.e. within Bluetooth range) or may occur continuously. Of course, it will be understood that the probe itself should include appropriate technology and hardware to communicate with the device.

The device may further include a user-interface to communicate information to the user. The device may further include a computer processor, data storage device, and/or associated hardware and software to receive and process raw data from the probe and provide information to the user based on the raw data. For example, rather than simply providing impendence measurements to the user, the device may interpret the raw data to provide information related to plant water status. Moreover, the device may retain and provide historical information for the plant to provide the user with an overview of changes in status overtime.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A system for real-time monitoring of plant status comprising:
    a probe comprising:
        a body that attaches to the plant; and
        a microprobe comprising a conductive gallium nitride tip that has been grown on top of a silicon needle body; and
        a device that receives the impedance measurements from the microprobe and provides information to a user based on the impedance measurements.

2. The system of claim 1 wherein the information that is delivered to the user is relative water content.

3. The system of claim 1 wherein the microprobe forms at least a part of the body that is attached to the plant.

4. The system of claim 1 further comprising an array of microprobes that measure impedance of the plant.

5. The system of claim 1 wherein the conductive tip has an effective diameter of between 10 nanometers and 10 micrometers.

6. The system of claim 1 wherein the conductive tip has an effective length of between 100 nanometers and 10 micrometers.

7. A method for measuring real-time plant status comprising:
- attaching, to a plant, a microprobe comprising a conductive gallium nitride tip and that has been grown on top of a silicon needle body;
- measuring impedance of the plant with the gallium nitride tip to obtain an impedance measurement;
- transmitting the impedance measurement to a user interface; and
- converting the impedance measurement into user-friendly data that provides plant status information to the user.

8. The method of claim 7 wherein the information that is provided to the user is relative water content.

9. The method of claim 7 wherein the plant status information includes historical information.

10. The method of claim 7 wherein the conductive tip has an effective diameter of between 10 nanometers and 10 micrometers.

11. The method of claim 7 wherein the conductive tip has an effective diameter of between 100 nanometers and 10 micrometers.

\* \* \* \* \*